United States Patent [19]

Weiner et al.

[11] Patent Number: 5,466,233
[45] Date of Patent: Nov. 14, 1995

[54] TACK FOR INTRAOCULAR DRUG DELIVERY AND METHOD FOR INSERTING AND REMOVING SAME

[75] Inventors: Alan L. Weiner, Cranbury, N.J.; Kevin Sinnett, Mukwonago, Wis.; Sterling Johnson, Skillman, N.J.

[73] Assignee: Escalon Ophthalmics, Inc., Skillman, N.J.

[21] Appl. No.: 232,895

[22] Filed: Apr. 25, 1994

[51] Int. Cl.[6] .................................................. A61M 35/00
[52] U.S. Cl. ....................................................... 604/890.1
[58] Field of Search .............................. 604/294, 890.1, 604/46, 892.1, 11

[56] References Cited

U.S. PATENT DOCUMENTS

| | | | |
|---|---|---|---|
| 3,828,777 | 8/1974 | Ness | 128/260 |
| 3,845,201 | 10/1974 | Haddad | 424/22 |
| 3,914,402 | 10/1975 | Shell | 424/32 |
| 3,926,188 | 12/1975 | Baker et al. | 604/294 |
| 3,949,750 | 4/1976 | Freeman | 604/294 |
| 3,995,635 | 12/1976 | Higuchi et al. | 128/260 |
| 4,014,335 | 3/1977 | Arnold | 128/260 |
| 4,034,758 | 7/1977 | Theeuwes | 128/26 |
| 4,135,514 | 1/1979 | Zaffaroni et al. | 128/260 |
| 4,164,559 | 8/1979 | Miyata et al. | 424/14 |
| 4,179,497 | 12/1979 | Cohen et al. | 424/22 |
| 4,186,184 | 1/1980 | Zaffaroni | 424/14 |
| 4,300,557 | 11/1981 | Refojo et al. | 128/260 |
| 4,343,787 | 8/1982 | Katz | 424/78 |
| 4,439,198 | 3/1984 | Brightman, II et al. | 604/894 |
| 4,634,418 | 1/1987 | Binder | 604/294 |
| 4,712,550 | 12/1987 | Sinnett | 128/334 R |
| 4,730,013 | 3/1988 | Bondi et al. | 524/42 |
| 4,774,091 | 9/1988 | Yamahira et al. | 424/426 |
| 4,851,228 | 7/1989 | Zentner et al. | 604/890.1 |
| 4,863,457 | 9/1989 | Lee | 604/891.1 |
| 4,979,938 | 12/1990 | Stephen et al. | 604/290 |
| 5,049,142 | 9/1991 | Herrick et al. | 604/294 |
| 5,098,443 | 3/1992 | Parel et al. | 623/4 |
| 5,141,748 | 8/1992 | Rizzo | 424/425 |
| 5,147,647 | 9/1992 | Darougar | 424/427 |
| 5,164,188 | 11/1992 | Wong | 424/428 |
| 5,171,270 | 12/1992 | Herrick | 623/11 |
| 5,238,687 | 8/1993 | Magruder et al. | 604/890.1 |
| 5,277,912 | 1/1994 | Lowe et al. | 604/890.1 |
| 5,334,189 | 8/1994 | Wade | 604/890.1 |

FOREIGN PATENT DOCUMENTS 0033042  8/1981  European Pat. Off. .

OTHER PUBLICATIONS

I. M. Katz et al., "A Soluble Sustained-Release Ophthalmic Delivery Unit", 8:5 (May 1977) pp. 728–734.

(List continued on next page.)

Primary Examiner—C. Fred Rosenbaum
Assistant Examiner—Manuel Mendez
Attorney, Agent, or Firm—Panitch Schwarze Jacobs & Nadel

[57] ABSTRACT

A tack for intraocular drug delivery and a method for insertion and removal of an intraocular device for sustained release of a drug are provided. The tack comprises a post, an anchoring region and a head. The post is for being positioned within the vitreous region of the eye. The post has a first end and a second end, and includes a drug to be administered. The anchoring region is affixed to the second end of the post, and includes a width measured perpendicularly to a longitudinal axis of the tack which varies to provide the anchoring region with a configuration to anchor the tack within at least one of a sclera, a retina and a choroid. The head extends radially outwardly from the anchoring region such that upon insertion of the anchoring region and post within the eye, the head remains external to the eye and abuts a scleral surface of the eye. Other embodiments include a tack comprising a post, a central portion, a head and a suture hole through the head for anchoring the head to the sclera. Alternatively the tack comprises a post having a first portion of liquid drug, a hollow central portion filled with a second portion of liquid drug in fluid communication with the post and a head with an opening which allows for injection of subsequent doses of liquid drug through the head into the central portion.

36 Claims, 4 Drawing Sheets

OTHER PUBLICATIONS

D. W. Lamberts, M.D. et al., "A Clinical Study of Slow-Releasing Artificial Tears", *Ophthalmology* 85 (1978) pp. 794–800.

P. Wright et al., "Slow-release Artificial Tear Inserts in the Treatment of Dry Eyes Resulting from the Oculomucocutaneous Syndrome", *British Journal of Ophthalmology* 67 (1983) pp. 393–397.

D. A. Lee et al., "Glaucoma Filtration Surgery in Rabbits Using Bioerodible Polymers and 5-Fluorouracil", *Ophthalmology* 94:12 (1987) pp. 1523–1530.

D. A. Lee et al., "The Use of Bioerodible Polymers and 5-Fluorouracil in Glaucoma Filtration Surgery", *Investigative Ophthalmology & Visual Science* 29–11 (1988) pp. 1692–1697.

T. Moritera et al., "Microspheres of Biodegradable Polymers as a Drug-Delivery System in the Vitreous", *Investigative Ophthalmology & Visual Science* 32–6 (1991) pp. 1785–1790.

G. E. Sanborn et al., "Sustained-Release Ganciclovir Therapy for Treatment of Cytomegalovirus Retinitis", *Arch. Ophthamol.* 110 (1992) pp. 188–195.

T. J. Smith et al., "Intravitreal Sustained-Release Ganciclovir", *Arch. Ophthamol* 110 (1992) pp. 255–258.

A. L. Weiner, "Chapter 13: Polymeric Drug Delivery Systems for the Eye", *Polymeric Site-Specific Pharmacotherapy*, pp. 315–346, Edited by A. J. Domb (1994) John Wiley & Sons Ltd.

C. W. Breslin et al., "Chapter 7. Slow Release Artificial Tears", *Symposium on Ocular Therapy* pp. 77–83.

TACK FOR INTRAOCULAR DRUG DELIVERY AND METHOD FOR INSERTING AND REMOVING SAME

FIELD OF THE INVENTION

The present invention relates to a tack for intraocular drug delivery and, more particularly, to a tack which may be anchored in at least one of the sclera, the retina and the choroid and which has a drug filled post to be inserted within the vitreous region of the eye. The present invention also relates to a method for insertion and removal of an intraocular device for sustained release of a drug into the vitreous region of the eye.

BACKGROUND OF THE INVENTION

For certain eye conditions and diseases, daily application of a therapeutic drug to the eye is disadvantageous and inconvenient. For these reasons, there have been many attempts to develop a device which delivers sustained release of ophthalmic drugs, is not susceptible to accidental ejection from the eye, does not cause undue discomfort to the patient receiving the drug and is a stable device which is easy to insert and remove.

Sustained delivery is accomplished in some of these devices which are extraocular inserts designed for placement inside the eyelid, external to the sclera, using tears manufactured in the eye to initiate diffusion of the drug across a membrane.

Earlier attempts at such a device include flexible ocular inserts adapted to be inserted in the conjunctival sac, the area of the eye bounded by the surfaces of the bulbar conjunctiva of the sclera and the palpebral conjunctiva of the lid. This device, known as OCUSERT™ is described in U.S. Pat. No. 3,828,777. This device has limitations due to varying patient tolerances which may cause retention difficulties resulting in patient pain, irritation and foreign body sensation. Problems with retention and irritation which may occur in the use of this device are documented, for example, in the following publications: P. Sihvola et al., "Practical Problems in the Use of Ocusert-Pilocarpine Delivery System", *Acta Ophthalmol. (Copenh.)*, December 1980, 58 (6) pp. 933–937; S. E. Smith et al., "Comparison of the Pupillary, Refractive and Hypotensive Effects of Ocusert-40 and Pilocarpine Eye Drops in the Treatment of Chronic Simple Glaucoma", *Br. J. Ophthalmol.*, April 1979, 63 (4) pp. 228–232; and I. P. Pollack et al., "The Ocusert Pilocarpine System: Advantages and Disadvantages", *South Med. J.*, October 1976, 69 (10), pp. 1296–1298.

In an attempt to reduce patient irritation and to improve anchoring of ocular drug delivery devices outside the sclera of the eye, devices which were capable of being retained in the fornix area of the conjunctival sac were also developed. Examples of such devices include a soluble mechanism which may be inserted in the inferior fornix as described in U.S. Pat. No. 4,164,559 and OCUFIT SR™ (previously named "SDRD") as described in U.S. Pat. No. 5,147,647. OCUFIT SR™ which is inserted in the fornix, is capable of sustained delivery for 7 or more days; however, it is somewhat vulnerable to ejection from the eye due to varying levels of patient tolerance.

In an attempt to avoid problems associated with extraocular inserts, there have been several devices developed for intraocular insertion into the vitreous region of the eye.

U.S. Pat. No. 4,300,557, for example, teaches a capsule which can be filled with a pharmaceutical drug to be delivered which serves as an intraocular implant. The capsule is inserted in the vitreous region of the eye by making an incision in the eye, inserting the capsule and closing the incision. The capsule remains in place for a period of time and may be removed by making a second surgical incision into the eye and retrieving the device. The capsule has an attached tube which passes through the surface of the eye and extends outward from the eye useful for the subsequent injection of a drug. While in the vitreous, the device is not anchored and may move about freely.

A similar device has been developed for insertion in the vitreous region of the eye and is described in T. J. Smith et al., *Intravitreal Sustained-Release Ganciclovir*, Arch. Opthalmol., 110, 255–258 (1992) and G. E. Sanborn, et al., *Sustained-Release Ganciclovir Therapy for Treatment of Cytomegalovirus Retinitis. Use of an Intravitreal Device*, Arch. Opthalmol., 110, 188–195 (1992). This device contains a cup-shaped encapsulated drug for sustained delivery. The cup-shaped portion of the device contains a strut having a suture hole for suturing the device to the eye once it is inserted in the vitreous. This device, like that of U.S. Pat. No. 4,300,557, is subject to movement within the vitreous due to a lack of an effective anchoring mechanism. It also must be removed by subjecting the patient to a second operative incision.

Other related devices are disclosed in U.S. Pat. No. 5,098,443 which describes a C-shaped ring capable of being inserted in and removed from the vitreous by two separate surgical incisions and which does not contain an anchoring mechanism and U.S. Pat. No. 4,712,500 which discloses a tack-like device capable of being inserted from the retinal tissue toward the outer surface of the eye useful for the reattachment of a detached retina. This tack device does not provide a means for sustained drug delivery. At the point of insertion, there is tissue destruction which may effect a scotoma, or blind spot, in the region of the eye where the device is inserted.

Therefore, while both intraocular and extraocular devices exist which allow sustained delivery of therapeutic drugs to the eye, a need still exists for a device which is easy to position, accomplishes controlled, sustained delivery of ocular drugs preferably to the posterior regions of the eye, particularly the vitreous region, but which is not vulnerable to unwanted ejection, does not cause undue patient irritation or discomfort, is stable within the vitreous region of the eye and is removable without requiring a second full thickness incision and further intrusive eye surgery.

SUMMARY OF THE INVENTION

The present invention provides a tack for intraocular drug delivery which, in one embodiment, comprises a post, an anchoring region and a head. The post includes a drug to be administered and has a first and second end. The first end is positioned within the vitreous region of the eye. The anchoring region is attached to the second end of the post and includes a width measured perpendicularly to the longitudinal axis of the tack. The width varies to provide a configuration to the anchoring region which anchors the tack in at least one of the sclera, the retina and the choroid of the eye. The head extends radially outwardly from the anchoring region such that upon insertion of the anchoring region and post within the eye, the head remains external to the eye and abuts the scleral surface of the eye.

In an alternative embodiment, the tack comprises a post, a central portion, a head and a suture hole. The post is the same as described above. The central portion is affixed to the second end of the post, and is for being positioned in at least one of the retina, the choroid and the sclera. The head extends radially outwardly from the central portion in the same manner described above. The suture hole extends through the head and may receive a suture to anchor the head to the sclera.

In another alternative embodiment, the tack comprises a post having a membrane, a hollow central portion and a head. The post has a first end and a second end. The membrane is at least semi-permeable and forms a hollow void. The void is filled with a first portion of a liquid drug to be administered. The first end of the post is for positioning in the vitreous region of the eye. The hollow central portion is affixed to the second end of the post and is filled with a second portion of the liquid drug to be administered. The void and hollow central portion are in fluid communication with one another. The central portion is for being positioned within at least one of the retina, the choroid and the sclera. The head extends from the central portion in the manner described above, and has an opening for injection of subsequent doses of the liquid drug. The opening is in fluid communication with the hollow central portion.

The invention further comprises a method for insertion and removal of an intraocular device for providing sustained release of a drug. The method comprises the steps of separating a portion of the conjunctival membrane of an eye from a portion of scleral tissue underlying the portion of the conjunctival membrane. An incision is made through the portion of scleral tissue into the vitreous region of the eye such that an opening for insertion of the device is created. The device is inserted into the opening such that a first portion of the device is situated in the vitreous region and a second portion of the device is positioned external to the portion of scleral tissue. The portion of the conjunctival membrane is reattached to the portion of the scleral tissue underlying the portion of the conjunctival membrane. The first portion of the device is maintained in the vitreous region until the first portion of the device has delivered a predetermined dosage of the drug into the vitreous region. The portion of the conjunctival membrane is separated from the portion of scleral tissue underlying the portion of the conjunctival membrane. The device is removed from the eye, and the portion of the conjunctival membrane is reattached over the opening in the portion of scleral tissue.

BRIEF DESCRIPTION OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, like numerals are used to indicate like elements throughout. In the drawings.

DETAILED DESCRIPTION OF PREFERRED EMBODIMENTS

Figure 1:
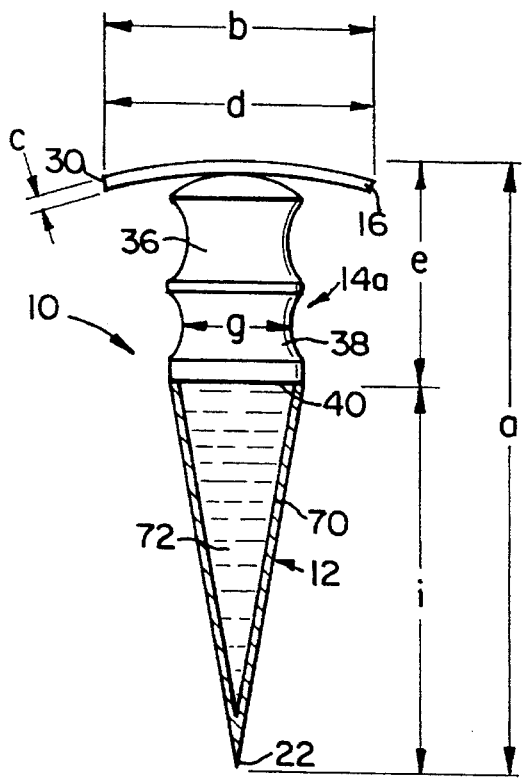
FIG. 1 is an elevational view of a tack for intraocular drug delivery in accordance with a first embodiment of the present invention.

The tack, generally designated 10, of the present invention comprises a post 12, a central portion 14 and a head 16. The central portion 14 may be configured as an anchoring region 14a for securing the tack 10 within the eye 18 as shown in FIGS. 1 to 5, 14 and 15, or the central portion 14 may be configured for ease of or frequent removal 14b as shown in FIGS. 8 to 12. In the embodiment in which the central portion 14 is configured for ease of removal 14b, the tack 10 is secured to the eye 18 by suture material (not shown) drawn through one or more suture holes 20 extending through the head 16a.

The post 12 may have various configurations. In first and sixth embodiments shown in FIG. 1 and 8, the post 12 is generally conical in shape, having a pointed first end 22. The pointed first end 22 allows the tack 10 to be inserted by puncturing the pointed first end 22 of the tack 10 into the eye 18 through the sclera 24 which is the outer fibrous layer of the eye 18. In the second through fifth and seventh through tenth embodiments of FIG. 2–5 and 9–12, respectively, the post 12 has a blunt first end 26. If the post 12 has a blunt first end 26, an incision is made into the eye 18 prior to inserting the tack 10, at the location designated for positioning of the tack 10.

The tack 10 is first described in terms of its general overall dimensions, followed by a description of suitable and preferred materials of construction, alternative embodiments of the posts 12 which may be used for different types of drug delivery and typical methods for manufacturing the tack 10.

A description of a preferred method for insertion and removal of a device such as the tack 10 from eye 18 follows the description of the tack 10.

As shown in FIG. 1, the length a of the tack 10 as measured along the longitudinal axis of the tack 10 preferably ranges from about 2.3 mm to about 30 mm. The overall width b of the tack 10 as measured perpendicularly to the longitudinal axis of the tack 10 ranges from about 1 mm to about 5 mm.

The head 16 of the tack preferably has a thickness and width which is sufficient to provide the head with enough structural integrity to prevent the tack from passing into the eye and yet thin enough to minimize sensation on the surface 28 of the sclera 24. The thickness c of the head 16 as measured along the longitudinal axis of the tack 10 is preferably from about 0.05 mm to about 2 mm, more preferably, the thickness c of the head 16 is 0.2. The diameter d, or width, of the head 16 as measured perpendicularly to the longitudinal axis of the tack 10 from one side of the edge 30 of the head 16 to the other side of the edge 30 of the head 16 is preferably from about 1 mm to about 5 mm, more preferably, the diameter d is from about 2 to about 4 mm. Preferably, d corresponds to the width b of the tack 10, because the head 16 is preferably wider than the central portion 14. It should be understood; however, that the tack 10 may be manufactured with a head 16 having a diameter d which is less than the overall width b of the tack 10 if the central portion 14 is wider than the head 16.

The central portion 14 of the tack 10 preferably has a length e measured along the longitudinal axis of the tack 10 of from about 0.25 mm to about 1 mm corresponding to the combined thicknesses of the retina 32 which is the nervous inner layer of the eye 18, the choroid 34 which is the vascular layer of the eye 18 and the sclera 24. The maximum diameter f, or width, of the central portion 14 measured perpendicularly to the longitudinal axis of the tack 10, whether configured as an anchoring region 14a or for ease of removal 14b, is from about 1 mm to 4 mm, more preferably, the maximum width f of the central portion 14 is from about 1 mm to about 3 mm. The maximum width f is preferably equal to or less than the width of the preferred area of insertion in the eye 18 corresponding to the general area of the ciliary pars plana 35 (the region between the ciliary pars plicata and the ora serrata) which is approximately 4 mm wide. The dimensions of the tack are preferably selected to complement the corresponding dimensions of an eye. The tack may be specially designed for a particular patient's eye size or manufactured in incremental sizes corresponding to various common patent eye dimensions.

When the central portion 14 is configured as an anchoring region 14a, the width g varies from a minimum width g of preferably from about 1 to about 3 mm to the maximum width f. The width g preferably varies to create a first portion 36 and a second portion 38 of the anchoring region 14a. The first portion 36 preferably appears generally concave when viewed from the side as shown in FIG. 1. The length of the first portion 36 preferably complements the thickness of the sclera 24. The second portion 38 preferably also appears generally concave when viewed from the side as shown in FIG. 1. The length of the second portion 38 preferably complements the combined thicknesses of the choroid 34 and retina 32. The first portion 36 and the second portion 38 of the anchoring region 14a may have other configurations (not shown) derived by, for example, varying the width g such that the portions 36, 38 appear convex when viewed from the side or by providing anchoring protrusions extending radially outwardly at any point along the length e of the anchoring region 14a. It will be understood by those skilled in the art that any potential configuration is contemplated which enables the anchoring region 14a to secure the tack 10 in the eye 18 by anchoring the central portion 14 of the tack 10 to at least one of the retina 32, the choroid 34 or the sclera 24 such that suturing is optional and movement of the tack 10 within the eye 18 once the tack 10 is in position is minimized. In addition, the anchoring region 14a should be configured to avoid damage to the eye 18 upon insertion or removal.

The post 12 preferably has a width, or diameter h, measured perpendicularly to the longitudinal axis of the tack 10 at the second end 40 of the post 12 of from about 1 mm to about 4 mm, more preferably from about 1 to about 3 mm. Like the central portion 14, the post 12 preferably has a diameter h less than or equal to the width of the ciliary pars plana. The length i of the post 12 as measured along the longitudinal axis of the tack 10, preferably varies from about 2 mm to about 27 mm. A length i of about 2 mm roughly corresponds to that portion of the vitreous 42 of the eye 18 which extends inwardly from approximately the area of the ciliary body 44 but which does not reach the lens 46. A length of from about 22 mm to about 27 mm corresponds to the distance measured between the juncture of the cornea 48 and the sclera 24, known as the sclerocorneal junction or limbus 50 to the furthest posterior retinal region 52 from the limbus 50. While the length i may be as high as approximately 27 mm in some cases, it is preferred that the maximum length i be in the range of from about 6 mm to about 7 mm to avoid any unnecessary obstruction of or obscuring of vision through the lens 46.

It should be understood that the length i of the post 12 is related to the quantity of drug to be delivered to the eye 18 and the duration of the sustained release. In addition, while it is preferred to use a maximum length i of from about 6 mm to about 7 mm to avoid obstructing vision, greater lengths having the potential for obstructing vision are appropriate in instances where serious ocular conditions such as those which may threaten blindness are to be treated and the pharmaceutical dosage requires a greater length i for the tack 10.

The head 16, which prevents the device from being inserted too far into the eye 18 and which aids in removal of the tack 10, may be constructed of any non-erodible biocompatible polymer. The polymer should be selected for flexibility and comfort of the patient to minimize the sensitivity of the scleral surface 28 to the tack 10. The polymer is preferably a silicone elastomer or silicone rubber, more preferably the polymer is polydimethyl siloxane or dimethyl diphenyl methylvinyl polysiloxane. Examples of other suitable non-erodible, biocompatible polymers which may be used include polyolefins such as polypropylene and polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, natural rubber, polyisobutylene, polymethylstyrene and other similar non-eroding biocompatible polymers known to those skilled in the art. This is a list of examples only, and should not be considered exhaustive.

Figure 6:
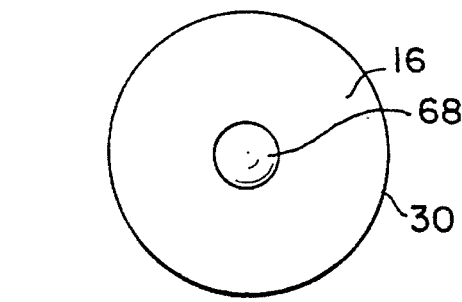
FIG. 6 is a top plan view of the tack shown in FIG. 5.
Figure 7:
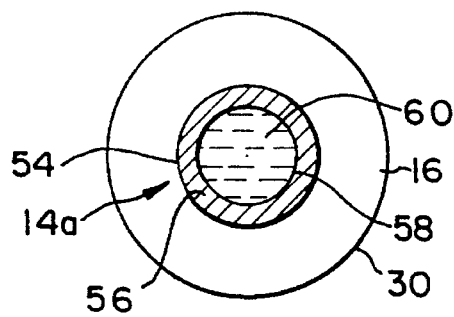
FIG. 7 is a cross-sectional view of the tack shown in FIG. 5 taken along line 7—7 of FIG. 5.
Figure 8:
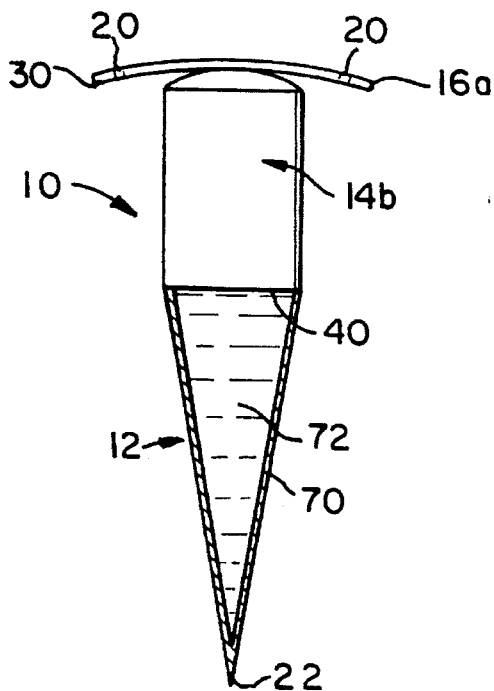
FIG. 8 is an elevational view of a tack for intraocular drug delivery in accordance with a sixth embodiment of the present invention.
Figure 13:
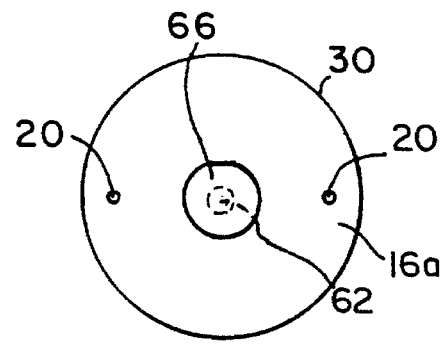
FIG. 13 is a top plan view of the tack shown in FIG. 12.

Preferably, the head 16 is generally flat. More preferably, the head 16 is generally flexible and curved to complement the curvature of the eye 18. When viewed from the top of the tack 10, the head 16 preferably appears generally circular in shape as shown in FIGS. 6, 7 and 13. The circular shape is preferred as there are no pointed edges which may irritate the eye, however, other shapes such as generally elliptical, square or triangular may be used for the head 16 and are within the scope of the present invention as long as the head 16 is configured to minimize irritation or risk of damage to the scleral surface 28.

If the central portion 14 of the tack 10 is configured for easy removal 14b as shown in FIGS. 8 through 12, the head 16 preferably comprises at least one suture hole 20 to anchor the tack 10 to the scleral surface 28. Preferably there are at least two suture holes 20 which are positioned approximately from about 0.05 mm to about 0.5 mm inward from any point along the edge 30 of the head 16. The two holes should preferably be on opposite sides of the head 16 or approximately 180° apart if the head 16 is generally circular, however, the positioning of the holes 20 is not critical. The suture holes 20 are preferably from about 0.1 to about 0.5 mm in diameter as measured perpendicularly to the longitudinal axis of the tack 10 and preferably extend longitudinally through the head 16.

The central portion 14 is preferably constructed of a non-erodible, biocompatible plastic such as a silicone elastomer or silicone rubber, more preferably, polydimethyl siloxane. The central portion 14 may also be constructed of any of the non-erodible, biocompatible materials which are listed above as suitable for constructing the head 16.

Figure 5:
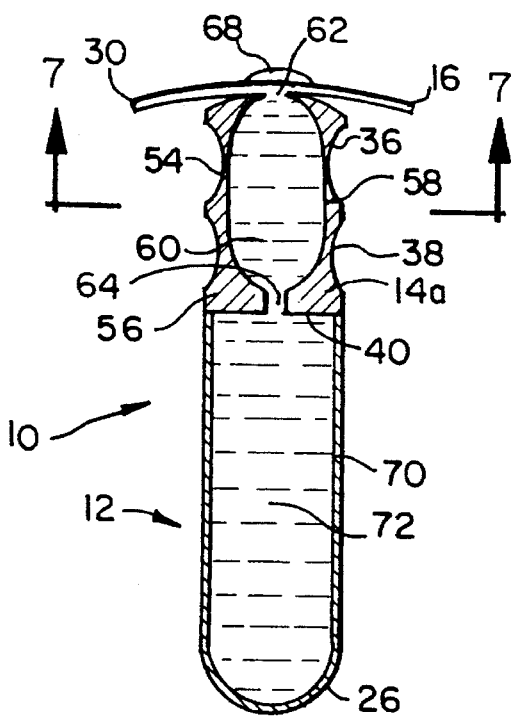
FIG. 5 is an elevational view of a tack for intraocular drug delivery in accordance with a fifth embodiment of the present invention.
Figure 12:
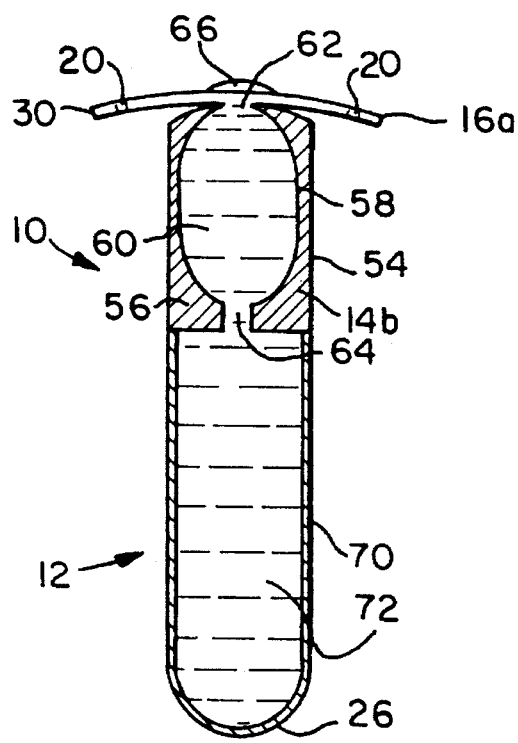
FIG. 12 is an elevational view of a tack for intraocular drug delivery in accordance with a tenth embodiment of the present invention.

The central portion 14 may be solid or hollow. If the central portion 14 is hollow, the central portion 14 may comprise an outer shell surrounding a void (not shown). Preferably, the central portion 14 is solid, having an exterior surface 54 and interior portion 56. A separate, hollow fluid chamber 58 may be positioned within the interior portion 56 as shown in FIGS. 5, 7 and 12. The hollow chamber 58 forms an interior space 60 for receiving subsequent dosages of a drug in liquid or gel form.

As shown in FIG. 12, the chamber 58 is preferably in fluid communication with both the post 12 and an opening 62 provided in the center of the head 16. As shown in FIGS. 5 and 12, the chamber 58 may be in fluid communication with the post 12 by providing a small conduit 64 extending from the hollow chamber 58, through the exterior surface 54 or outer shell of the central portion 14 into the post 12. The conduit 64 may optionally comprise a one-way valve or diaphragm for flow control (not shown). The opening 62 as shown in FIGS. 12 and 13 may be covered by a removable sterile cap 66. The cap 66 may also be attached in a hinged fashion to the head 16, however, attachment is not necessary.

Preferably, instead of an opening 62 and a cap 66, the chamber 58 is accessible through the head 16 by an injection port 68 of any type known to those of ordinary skill in the art as shown in FIGS. 5 and 6. The injection port 68 may be any puncturable membrane and is preferably constructed of, for example, a silicone rubber, a silicone elastomer or a polyolefin. A drug in liquid or gel form may be injected through the injection port 68 without unnecessary exposure to the external environment thereby aiding in the prevention of infection from subsequent injections of the drug.

The post 12 may be one of several different preferred embodiments described herein. These embodiments are for descriptive purposes, and should not be considered as limiting. While it is preferred that the post 12 be generally conical as shown in FIGS. 1, 8, 14 and 15 or capsule-shaped as shown in FIGS. 2 to 5, the post 12 may have any configuration or shape. The post 12 may also be made of varied materials known to those skilled in the art, in addition to those described below, as long as the post 12 extends from the central portion 14 into the vitreous 42 of the eye 18 and is capable of providing a means for sustained, controlled delivery of drugs to the vitreous 42 of the eye 18.

The mechanisms for sustained, controlled drug release into the vitreous 42 of the eye 18 preferably include diffusion, osmosis, erosion, dissolution and combinations of these mechanisms. However, any suitable mechanism known to those skilled in the art which accomplishes sustained, controlled release of a drug into a substantially liquid medium such as the vitreous 42 may be used with the tack 10 of the present invention. The period of sustained release is, for example, at least 3 days, and preferably more than 14 days. In cases including the treatment of diseases such as AIDS-related cytomegaloviral infections, periods of up to 6 months for sustained release are preferred. With respect to the embodiment of the tack 10 which includes a refillable chamber 58 as shown in FIGS. 5, 7 and 12, the sustained release of the drug into the eye 18 may be extended for an indefinite period of time.

In one preferred embodiment as shown in FIGS. 1, 5, 8 and 12, the post 12 comprises a outer membrane 70 which may be permeable or semi-permeable. The membrane 70 forms a cavity 72. The cavity is filled with a drug in liquid or gel form to be administered. The water in the vitreous 42 swells the membrane 70 allowing the drug to pass through the membrane 70 by a mechanism such as, for example, osmosis or diffusion into the vitreous 42.

Figure 4:
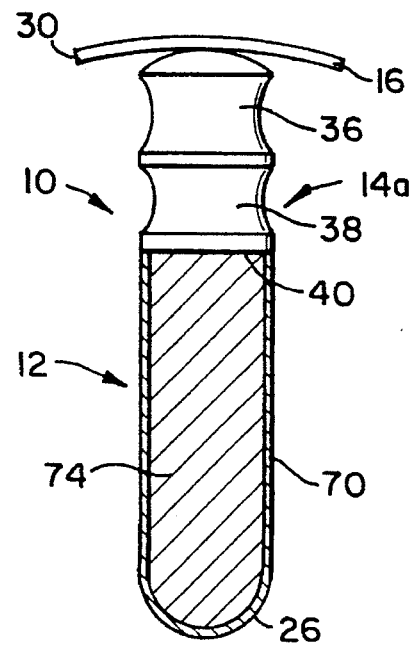
FIG. 4 is an elevational view of a tack for intraocular drug delivery in accordance with a fourth embodiment of the present invention.
Figure 11:
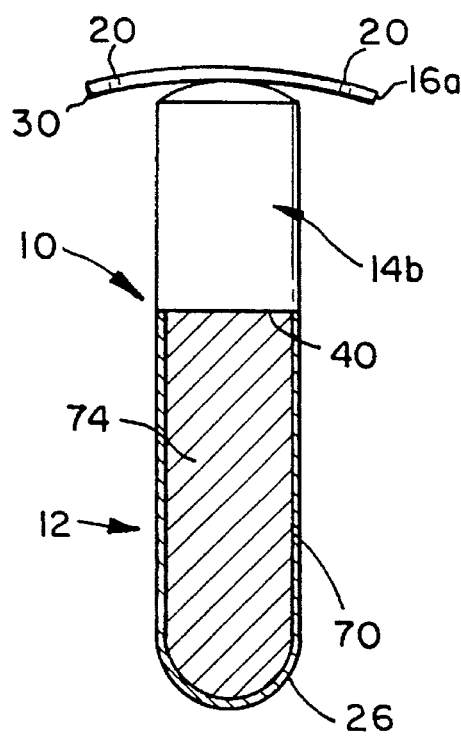
FIG. 11 is an elevational view of a tack for intraocular drug delivery in accordance with a ninth embodiment of the present invention.

As shown in FIGS. 4 and 11, the membrane 70 may also surround a solid drug core 74. The solid drug core 74 would dissolve in the water absorbed from the vitreous 42 and then pass through the membrane 70 into the vitreous 42 by, for example, either diffusion or osmosis.

Figure 2:
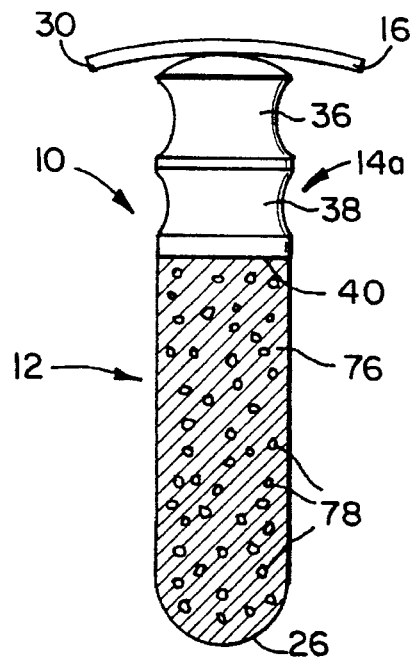
FIG. 2 is an elevational view of a tack for intraocular drug delivery in accordance with a second embodiment of the present invention.
Figure 9:
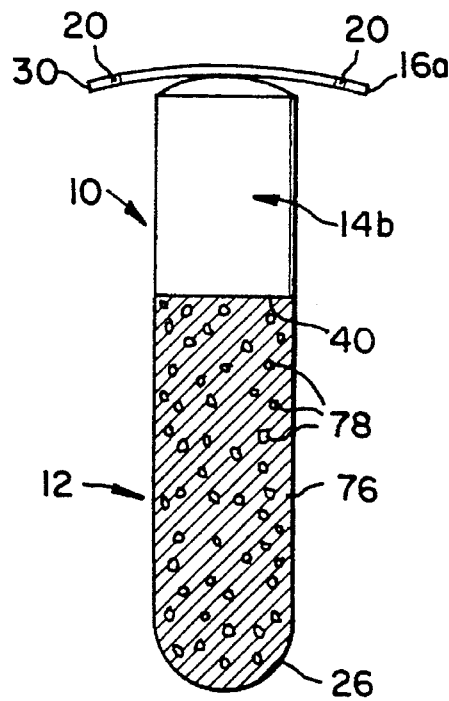
FIG. 9 is an elevational view of a tack for intraocular drug delivery in accordance with a seventh embodiment of the present invention.

As shown in FIGS. 2 and 9, the post 12 may also comprise a solid, non-erodible polymeric matrix 76 having drug particles 78 dispersed within the matrix 76. The matrix 76 is preferably porous. The drug particles 78 diffuse through the matrix 76 into the vitreous 42.

Figure 3:
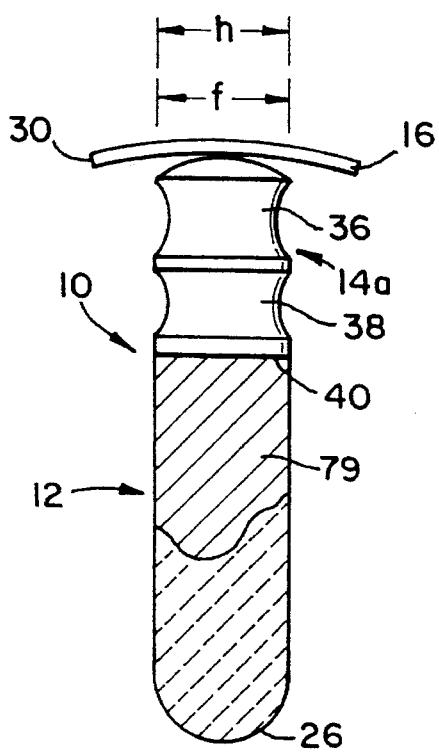
FIG. 3 is an elevational view of a tack for intraocular drug delivery in accordance with a third embodiment of the present invention.
Figure 10:
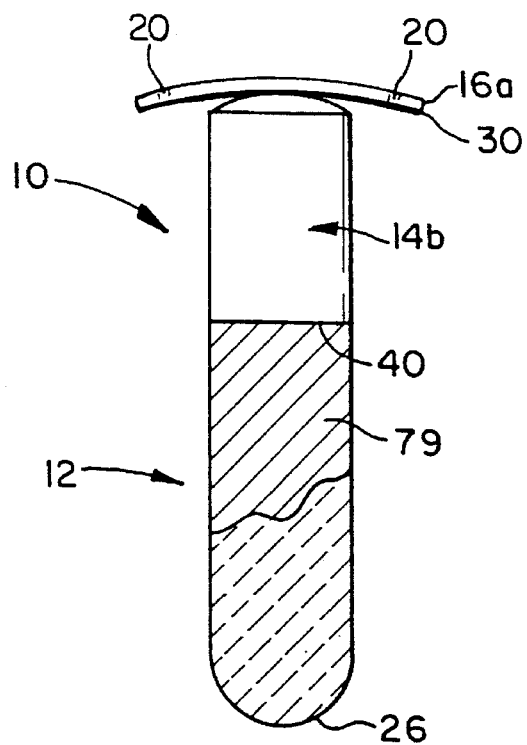
FIG. 10 is an elevational view of a tack for intraocular drug delivery in accordance with a eighth embodiment of the present invention.

The drug may also be dissolved in a solid, erodible polymer 79 as shown in FIGS. 3 and 10. In this embodiment, the drug is delivered to the vitreous 42 by dissolution or bio-erosion of the post 12 as shown by the phantom lines in FIGS. 3 and 10.

Examples of permeable materials which may be used for the membrane 70 include microporous, biocompatible materials, preferably insoluble in the material of the vitreous 42 comprised of, for example, polycarbonates; polyvinyl chlorides; polyamides such as polyhexamethylene adipamide and nylons; copolymers of polyvinyl chloride and acrylonitrile; polysulphones; polyvinylidene fluorides; polyvinyl fluorides; polychloroethers; formaldehyde resins; acrylic resins such as polyacrylonitrile, polymethylmethacrylate and poly(n-butyl methacrylate); polyurethanes; polyimides; polybenzimidazoles; polyvinyl acetate; polychloroethers; polyethers; cellulose esters such as cellulose triacetate; porous rubber; cross-linked poly(ethylene oxide); cross-linked polyvinylpyrrolidone; cross-linked poly(vinyl alcohol), polystyrenes such as poly(sodium styrenesulfonate); cellulose; colloidion and gelatin.

The permeable membrane 70 allows for the drug in liquid or gel form to pass through the membrane 70 into the vitreous 42 by a diffusion mechanism. In addition, if there is a solid drug core 74, the solid may dissolve in water absorbed through the membrane 70 from the vitreous 42 and then diffuse through the membrane 70 with the water as a diffusion carrier. Diffusion allows for continuous drug release at a controlled rate. Preferably, if the drug is in a liquid or gel form, it is suspended in a diffusion medium which also serves as a pharmaceutical carrier. The active ingredient of the drug may be suspended or dissolved in the diffusion medium. The active ingredient is preferably of a limited solubility in the medium. Examples of suitable diffusion media include saline, glycerin, ethylene glycol, propylene glycol, water with or without suspension or emulsifying agents, mixtures of propylene glycol monostearate and oils, gum tragacanth, sodium alginate, poly(vinyl pyrrolidone), polyoxyethylene stearate, fatty acids, silicone oil and similar materials.

Examples of semi-permeable, biocompatible materials useful for forming the membrane 70 include cellulose acetate and its derivatives, partially and completely hydrolyzed copolymers of ethylene-vinyl acetate, highly plasticized polyvinyl chloride or nylon, homopolymers and copolymers of polyvinyl acetate, polyesters, homopolymers and copolymers of acrylic acid and methacrylic acid, polyvinylalkylethers, polyvinyl fluoride, silicone polycarbonates, aromatic nitrogen-containing polymeric membranes, polymeric epoxides, copolymers of alkylene oxide and silylglycidylether, polyurethanes, polyglycolic or polyacetic acid and derivatives thereof, derivatives of polystyrene such as poly(sodium styrenesulfonate) and poly(vinyl benzyltrimethyl-ammonium chloride).

A semi-permeable membrane 70 preferably allows delivery of the drug in solid or liquid form to the vitreous 42 by the mechanism of osmosis. If a solid drug core 74 is used, the drug may dissolve in water which passes inwardly through the membrane 70. The water provides osmotic pressure allowing the drug to pass outwardly through the semi-permeable membrane 70. In a typical osmotic mechanism, a drug in liquid or gel form is dissolved in a solute which cannot pass through the membrane 70. Examples of suitable solutes which can be used with a drug in the post 12 and which cannot pass through a semi-permeable membrane 70 in an osmotic mechanism include water-soluble inorganic and organic salts and compounds such as magnesium sulfate, magnesium chloride, sodium chloride, lithium chloride, potassium sulfate, sodium carbonate, sodium sulfate, lithium sulfate, calcium bicarbonate, calcium sulfate, potassium acid phosphate, calcium lactate, magnesium succinate, tartaric acid, acetamide, choline chloride and soluble carbohydrates such as sorbitol, mannitol, raffinose, glucose, sucrose and lactose.

If a solid, non-erodible polymeric matrix 76 having drug particles 78 dispersed within the matrix 76 is used as the post 12 (see FIGS. 2 and 9), the matrix 76 may comprise any of the non-erodible, biocompatible polymers described above. As the matrix 76 is preferably porous, the drug 78 may be released by diffusing through the pores (not shown) in the matrix 76. Controlled, sustained release may be regulated by the gradual dissolution of the dispersed drug particles 78 within the matrix as a result of inward diffusion of water from the vitreous 42. Preferably, the matrix 76 is a silicone elastomer or silicone rubber such as a polydimethyl siloxane.

Referring now to FIGS. 3 and 10, if the drug is dissolved or otherwise dispersed in a bio-erodible polymer matrix 79, contact of the post 12 with the vitreous results in a controlled, sustained release by bioerosion of the matrix 79 with the drug therein. The drug may be dispersed uniformly throughout the matrix 79, however, preferably, the drug is superficially concentrated in the matrix for a more controlled release. Examples of bio-erodible materials for the matrix 79 include polyesters of molecular weight from about 4,000 to about 100,000, homopolymers and copolymers of polylactic acid and polyglycolic acid, polycaprolactone, homopolymers and copolymers of polyanhydrides such as terephthalic acid anhydride, bis(p-anhydride) and poly(p-carboxyphenoxy) alkyl, homopolymers and copolymers of dicarboxylic acids such as sebacic, adipic, oxalic, phthalic and maleic acid, polymeric fatty acid dimer compounds such as polydodecanedioic acid polyorthoesters, poly(alkyl-2-cyanoacrylate) such as poly(hexyl-2-cyanoacrylate), collagen (gelatin), polyacetals, divinyloxyalkylenes, polydihydropyrans, polyphosphazenes, homopolymers and copolymers of amino acids such as copolymers of leucine and methyl glutamate, polydioxinones, polyalkylcyano acetates, polysaccharides and their derivatives such as dextran and cyclodextran, cellulose and hydroxymethyl cellulose.

The tack 10 of the present invention may be used for controlled, sustained release of drugs for treating a variety of ocular diseases such as, for example, retinal detachment, proliferative retinopathy, proliferative diabetic retinopathy, degenerative disease, vascular diseases, occlusions, infection caused by penetrating traumatic injury, endophthalmitis such as endogenous/systemic infection, post-operative infections, inflammations such as posterior uveitis, retinitis or choroiditis and tumors such as neoplasms and retinoblastoma.

Examples of ophthalmic drugs which may be delivered by the tack 10 of the present invention include antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; antibacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluorometholone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol Hcl and betaxolol Hcl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors. Other drugs known to those skilled in the art which are capable of controlled, sustained release into the eye 18 in the manner described herein are also suitable for use in the present tack 10.

The drugs may be used in conjunction with a pharmaceutically acceptable carrier such as, for example, solids such as starch, gelatin, sugars, natural gums such as acacia, sodium alginate and carboxy-methyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil and the like, with emulsifiers such as mono- or di-glyceride of a fatty acid, or a phosphatide such as lecithin, and the like; glycols and polyalkylene glycols; aqueous media in the presence of a suspending agent, for example, sodium carboxy-methylcellulose, sodium alginate, poly(vinyl pyrrolidone) and similar compounds, either alone, or with suitable dispensing agents such as lecithin, polyoxyethylene stearate and the like. The carrier may also contain adjuvants such as preserving, stabilizing, wetting, emulsifying agents or other related materials.

The tack 10 may be manufactured in accordance with typical methods of extrusion or injection molding known to those of ordinary skill in the art. Preferably, a silicone rubber for the head 16 and central portion 14 is used. A silicone rubber material may be prepared, for example, by mixing a dimethylsiloxane polymer or dimethyl and methylvinyl siloxane copolymers, reinforcing silica, a platinum catalyst, one or more inhibitors and siloxane cross-linking agents and other vulcanizing agents such as, for example, organic peroxides.

Polymeric materials used as a base material for molding either the head 16, the central portion 14 or the post 12 may be either hand mixed, mixed on a two-roll mill, or injection molded for drug loading. In molding a post 12, the drug may be added to an erodible or non-erodible polymeric matrix material 76, 79 by admixing the drug either simultaneously with the component or components of the polymeric matrix material or after components of the polymeric matrix material have been blended. The drug is generally added at levels of up to about 40% by weight of the total weight of the mixture of drug and silicone rubber including any necessary excipients or release modifiers such as, for example, glycerin or sorbitol, however, larger quantities of drug may be loaded into the matrix depending upon the nature of the matrix and the drug to be loaded.

Air which may be entrapped in the mixture is removed by exposure to a vacuum of about 28 inches of mercury for approximately 30 minutes. The drug is solidified within the polymeric matrix by curing and molding the mixture into the desired shape. Any typical process known to those of ordinary skill in the art may be used for molding a polymeric matrix to form the shape of the desired central portion 14, head 16 or post 12 of the tack 10 or for molding an erodible or non-erodible polymeric matrix material comprising a drug into the desired post 12 shape including, for example, extrusion molding, injection molding and compression molding.

If injection molding is used, the polymeric material, with or without the loaded drug, is placed into a heated press (not shown) with a metallic mold made of, for example, aluminum or stainless steel which contains impressions of each component portion of the tack 10 and its corresponding size. The mixture is forced into the mold at a pressure of between about 200 and 4,000 psi. The mold is preferably kept under a pressure of about 10 tons by clamping. Heat is preferably provided in varying degrees for varying periods of time to the filled mold to form a particular head 16, central portion 14 or post 12. Examples of typical combinations of molding time periods and temperatures used in molding the head 16, central portion 14 or post 12 of the tack 10 are included in Table I below.

TABLE I

| Molding Time (minutes) | 4–10 | 15 | 30 | 120 | 300 |
|---|---|---|---|---|---|
| Molding Temperature (°C.) | 135 | 100 | 75 | 55 | 40 |

The mold is then cooled and separated. The formed pieces are removed from the mold. As an alternative to the application of heat and pressure, the material may be cured at approximately 25° C. for a period of about 24 or more hours. After the pieces are cured, cooled and removed from the mold, they are assembled by using a sterile medical grade adhesive such as for example, Silastic® 7-2947 Medical Adhesive Type A, Sterile available from Dow Corning Corp., Midland, Mich. Other suitable medical adhesives known to those of ordinary skill in the art are within the scope of this invention. The adhesive is allowed to cure at room temperature and at a minimum relative humidity of about 20%.

If extrusion molding operations are used, the polymeric material is blended alone or with a drug which may be added simultaneously with the polymeric material or after blending the polymeric material. The drug is added in amounts of up to about 40% by weight of the total mixture if a post 12 is to be formed which includes a drug to be loaded in an erodible or non-erodible polymeric matrix. Blending is carried out on a cooled two-roll mill and the material is fed into a single screw extruder (not shown). The single screw preferably has diminishing pitch and a range of length to diameter ratios of from about 12:1 to about 10:1. The material is continuously forced out as extrudate through a coin or plate die (not shown) with openings conforming to the shape and dimensions of the cylindrical portion of the head 16, central portion 14 or post 12 of the tack 10. A mandrel (not shown) held in place by a spider flange (not shown) may be positioned prior to the die for certain post 12 configurations.

The continuous extrudate is pulled via a conveyer belt (not shown) through a heated chamber (not shown) in order to vulcanize the material. The chamber may be of any type typically used by those of ordinary skill in the art and may be horizontal or vertical. The chamber is preferably heated to from about 315° C. to about 425° C. The final head 16, central portion 14 or post 12 of the tack 10 is made by cutting the vulcanized extrudate to size by any means known to those of ordinary skill in the art. Modifications such as polishing or sharpening the ends of the post 12 or subsequent molding of portions of the tack 10 may be performed after cutting the extrudate to size.

Compression molding may also be used for certain polymeric matrices such as, for example, solid mixtures of erodible polymers such as polyhydroxy acids including polylactic acid, polyglycolic acid and polyhydroxybutyrate; polyesters and polyorthoesters including cyclic orthoesters with diols or diketeneacetals and diacids with diols or polyols; polyanhydrides made from, for example, p-carboxyphenoxy propane, p-carboxyphenoxy hexane, sebacic acid, dodecanedioic acid, 1,4-phenylenedipropionic acid, isophthalic acid, polypropylene fumarate, polypropylene maleate and mixtures of these polyanhydrides; polypeptides; and polycyanoacrylates.

When forming a post 12, these polymeric matrices may be admixed with up to 60% by weight of a particular drug to be delivered. The polymeric/drug matrix mixture may be compressed in a metallic mold made of, for example, aluminum or stainless steel, situated in a press such as, for example, a Carver® hydraulic press under 12 tons of pressure for at least about 15 minutes at a temperature of about 100° C. The mold is then cooled and separated as described above. The post 12 is removed and assembled with other portions of the tack 10 by use of a medical adhesive cured as described above.

It should be understood in practicing any of the above-described molding methods that a drug may or may not be loaded in any of the component pieces of the tack 10 including the head 16, the central portion 14 or the post 12. While it is preferred to include the drug only in the post 12 to better manage the sustained controlled release of a drug, it is acceptable to have a drug molded in the head 16 or central portion 14 as an alternative method of manufacturing.

The manufacture of the present invention will now be more fully described in accordance with the following nonlimiting examples.

EXAMPLE I

A placebo device and a hollow refillable device for use with a liquid drug are made by using one part Silastic® MDX4-4210 curing agent available from Dow Corning Corp., Midland, Mich. and 10 parts of MDX4-4210 Silastic® base elastomer also available from Dow Corning Corp., Midland, Mich. The mixture is placed under a vacuum of 28 inches of mercury for 30 minutes.

The mixture is then transferred to the cylinder of a transfer press. The mixture is forced into an aluminum mold heated to 135° C. which contains separate impressions of the head 16 with an opening for an injection port 68, a head 16 without an opening, an anchoring region 14a with a void 58, an anchoring region 14a without a void 58, and a post 12 with a pointed end 22. The material is forced into the mold at a transfer pressure of 400 psi. The mold is kept under a 10 ton clamp pressure. The material remains in the mold for a period of 3.5 minutes after which the mold is cooled to room temperature and separated.

The formed portions of the tack 10 are removed from the mold. Flashing is trimmed and polished. The head 16 with injection port 68 opening, a rubber insert for an injection port 68 as well as the anchoring region 14a with void 58 and a separately-molded hollow, cellulose membrane post 12 are assembled in the manner shown in FIG. 5 by binding the pieces together using the adhesive, Silastic® 7-2947 Medical Adhesive Type A, Sterile available from Dow Corning Corp., Midland, Mich. thereby forming a refillable device. The anchoring region 14a without a void 58, the head 16 without an opening for an injection port 68 and the pointed post 12 are also assembled with the Silastic® adhesive forming a placebo device. The adhesive in both devices is cured at room temperature and a minimum relative humidity of 20%. The refillable device is then filled with any suitable liquid drug together with a pharmaceutically acceptable carrier.

EXAMPLE II

A tack having a drug-loaded post 76 is manufactured by mixing one part of Silastic® MDX4-4210 curing agent with 10 parts of MDX4-4210 Silastic® base elastomer. Oxytetracycline hydrochloride available from Sigma Chemical Company, St. Louis, Mo. is blended into the elastomeric mixture in an amount equal to 20% by weight of the total mixture. Care is taken to minimize the entrapment of air in the mixture during blending.

The mixture is placed under a vacuum of 28 inches of mercury for 30 minutes. The mixture is transferred into the cylinder of a transfer press, where it may be forced into an aluminum mold heated to 121° C. which contains a separate impression of the post 76 of the device. The mold is kept under 10 tons of clamp pressure for 3.25 minutes at which time the mold is cooled to room temperature and separated.

The formed post 76 of the tack 10 is removed from the mold. Flashing is trimmed and polished. The drug-loaded post 76 is assembled by using the adhesive, Silastic® 7-2947 Medical Adhesive Type A, Sterile to a non-drug-loaded head 16 and anchoring region 14a formed in accordance with the method described in Example I. The adhesive is cured at room temperature and a minimum relative humidity of 20%.

Figure 14:
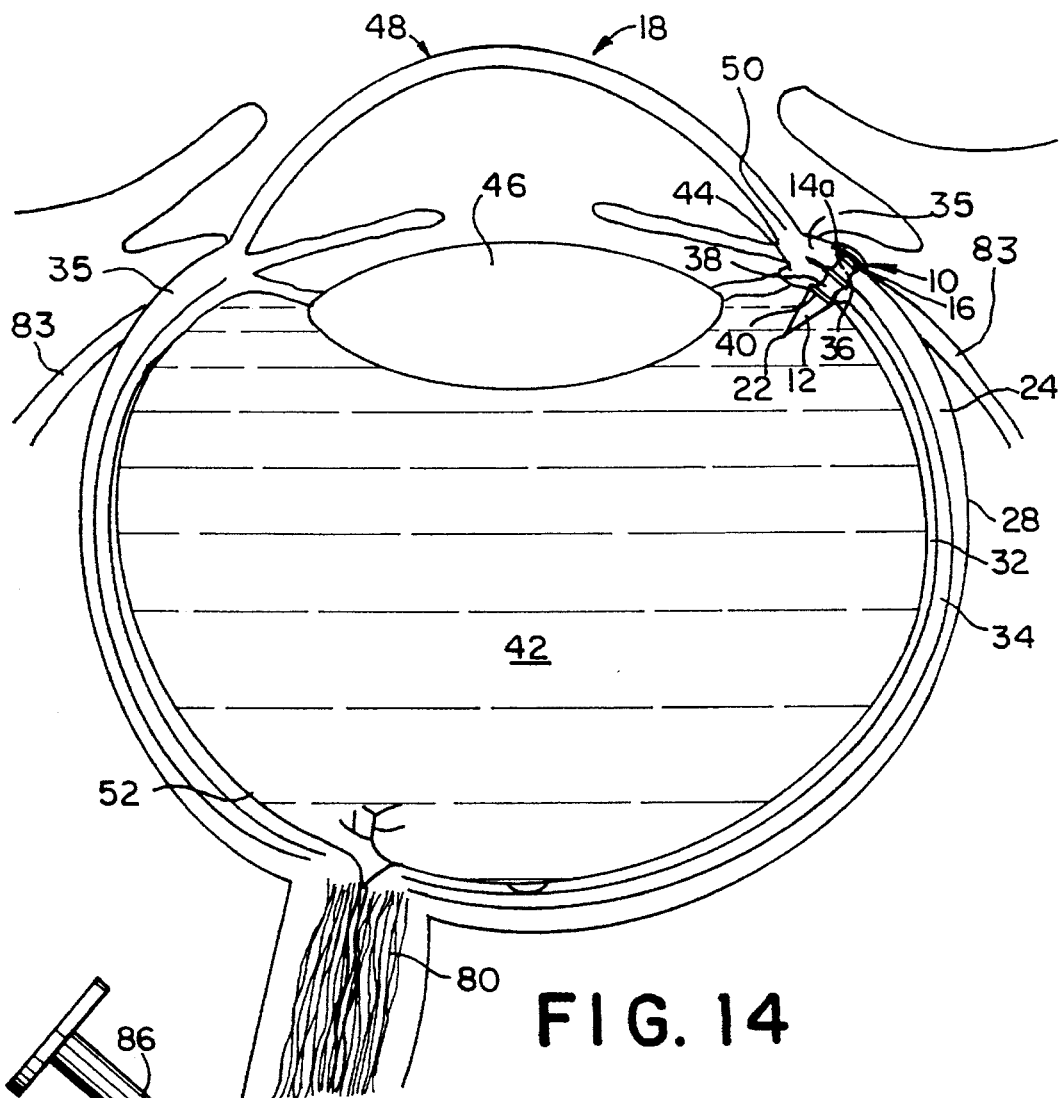
FIG. 14 is a cross-sectional view of an eye having the tack shown in FIG. 1 positioned therein.

As shown in FIG. 14, the tack 10 of the present invention is preferably inserted into those portions of the sclera 24 on either side of the eye 18 posterior to the ciliary bodies 44 known as the ciliary pars plana 35. The tack 10; however, is suitable for insertion at any point along the sclera 24. The length e of the central portion 14 should correspond to the varying thicknesses of the sclera 24 at the point of insertion. The scleral 24 thickness varies from its thinnest, about 0.4 mm measured about 6 mm posterior to the limbus 50, to its thickest, about 1 mm measured near the entrance of the optic nerve 80. Preferably, the tack 10 is placed such that it does not obscure vision through the lens 46. In addition, placement of the tack 10 nearer to the ciliary body 44 as opposed to a more posterior location has the advantage of an easier insertion since the area around the ciliary body 44 is accessible from the front of the eye 18.

A method of insertion and removal of an intraocular device will now be described with respect to a preferred embodiment in which the tack 10 of the present invention is inserted into and removed from the eye 18. It should be understood by one of ordinary skill in the art that the method of insertion and removal described may be practiced with any other intraocular device which comprises a drug containing portion to be fully inserted into the vitreous 42 region of the eye 18 and a portion which remains external to the scleral surface 28 without departing from the scope of this invention.

In preparation for insertion of the tack 10 into the eye 18, the patient is anaesthetized with a general and/or a retrobulbar plus lid block. The lids are retracted. A small conjunctival flap (not shown) is made exposing the sclerocorneal limbus 50. The flap must be at least as large as the diameter d of the head 16. The flap may be fornix based by incising the conjunctival-Tenons layer at the sclerocorneal limbus 50 with dissection superiorly toward the superior rectus muscle 83. Bleeding vessels and the site around the planned entry point on the scleral surface 28 are cauterized.

The eye 18 is entered with a 20 G microvitreoretinal blade (not shown) by holding it generally perpendicular to the eye 18, aiming toward the anatomical center of the globe of the eye 18, entering the eye 18 to completely penetrate the pars plana 35, and visualizing the knife tip (not shown) through the pupil to verify penetration thereby creating a full thickness incision of a length preferably slightly smaller than the width b of the tack 10. The tack 10 is then inserted through the incision. A slight twirling motion is preferred during insertion to facilitate entry. In tacks 10 with suture holes 20, 9-0 or 10-0 nylon sutures are used to secure the head 16a to the sclera 24. The conjunctival flap is closed and secured with 7-0 or 8-0 polyglactin sutures such as, for example, Vicryl®.

Figure 15:
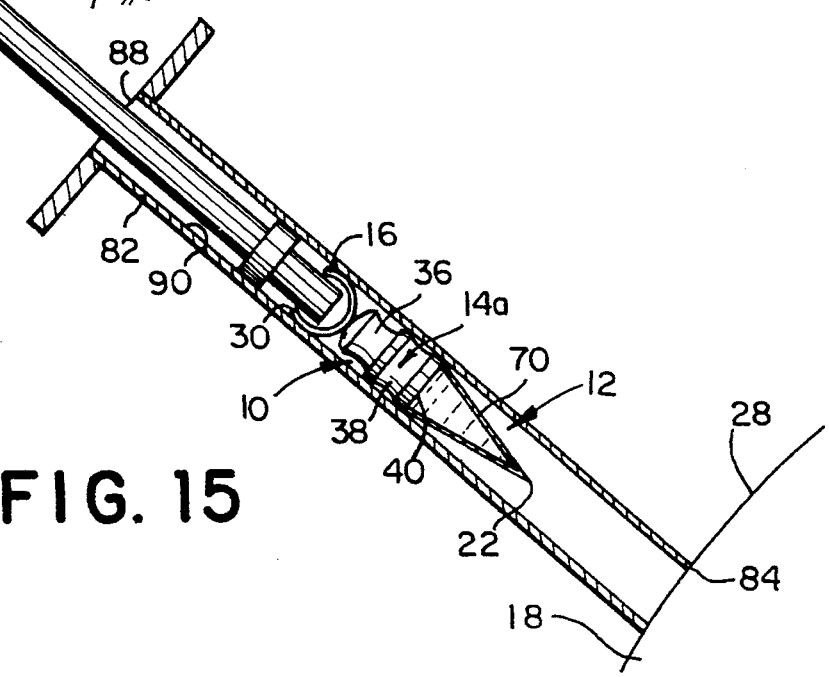
FIG. 15 shows a syringe for injecting the tack of the present invention into the sclera of the eye.

In the preferred method of insertion, the tack 10 of the present invention is inserted into the eye 18 by injection. While the tack 10 may be inserted by hand into the sclera 24, injection is preferred as it helps to prevent risk of accidental damage or abrasion to the scleral surface 28. In addition, injection provides for a substantially straight insertion. As shown in FIG. 15, the tack 10 may be injected by loading the tack 10, with the first end 22, 26 of the post 12 pointed toward a first end 84 of the syringe 82 and the head 16 abutting the plunger 86 of the syringe 82 when the plunger is in a fully extended position.

The syringe 82 preferably has a width which is at least as wide as the width h of the post 12 or the maximum diameter h of the central portion 14 of the tack 10, but which is equal to or less than the diameter d of the head 16. The head 16, which is preferably flexible, will then at least partially flex backward toward the second end 88 of the syringe 82 providing some frictional resistance between the interior surface 90 of the syringe 82 and the head 16. Some resistance is preferred for better control over the injection of the tack 10. In cases where the diameter d of the head 16 is not greater than the diameter h of the central portion 14 or than the width h of the post 12, the syringe 82 is preferably only slightly wider than the widest portion of the tack 10 such that some resistance occurs between the tack 10 and the interior surface 90 of the syringe 82, but the tack 10 moves through the syringe 82 without sticking or requiring excessive pressure.

The first end 84 of the syringe 82 is positioned such that it abuts the scleral surface 28 as shown in FIG. 15. The plunger 86 is then pressed inwardly toward the scleral surface 28 under a steady application of force until the first end 22, 26 of the post 12 passes through the scleral surface 28 and enters the vitreous 42 and the head 16 abuts the scleral surface 28. The syringe 82 is then withdrawn. If the tack 10 has a central region 14b which is configured for ease of removal, suture material (not shown) is used to secure the head 16a to the eye 18 by drawing through the suture holes 20. An optional small incision may be made in the manner described above prior to injection of the tack 10 to facilitate insertion if the post 12 has a pointed end 22. If the post 12 has a blunt end 26, then a small incision as described above should be made prior to insertion. After insertion, conjunctival flap should be closed with stitches as described above or by any method known to those of ordinary skill in the art.

The tack 10 remains in the eye 18 until the patient no longer requires the tack 10 due to full delivery of the required dosage over a predetermined period of time. At this point, the tack 10 is removed from the eye by making a small conjunctival flap in the manner described above with respect to preparation for insertion of the tack. After the head 16 of the tack is exposed, the physician may simply remove the tack and close the conjunctival flap without making a further full thickness incision into the vitreous region 42 of the eye 18 to retrieve the tack 10.

If suture material is still present, the sutures must be removed by any means known to those of ordinary skill in the art prior to removing the tack 10. The tissue originally enclosing the tack 10 while the tack 10 is inserted should close naturally after removal of the tack 10 even if an anchoring region 14a is used. A suture may be required to close the surface of the sclera over the opening remaining after removal of the tack 10 while the tissue is still healing.

It will be appreciated that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A tack for intraocular drug delivery, comprising:

(a) a post including a drug to be administered, the post having a first end and a second end, the first end for being positioned within a vitreous region of an eye, the post having a length measured parallel to a longitudinal axis of the tack, the length being determined according to a dosage of the drug to be administered and such that obstruction of vision through a lens of the eye is minimized;

(b) an anchoring region affixed to the second end of the post, the anchoring region including a width measured perpendicularly to the longitudinal axis of the tack, said width varying to provide the anchoring region with a configuration which anchors the tack within at least one of a sclera, a retina and a choroid; and (c) a head extending radially outwardly from the anchoring region such that upon insertion of the anchoring region and post within the eye, the head remains external to the eye and abuts a scleral surface of the eye.

2. The tack according to claim 1, wherein the anchoring region is divided into a first portion and a second portion, the first portion of the anchoring region having a first width measured perpendicularly to a longitudinal axis of the tack and the second portion of the anchoring region having a second width such that the first width varies to create a first concave section in the first portion of the anchoring region and to secure the first portion within the choroid and the retina and the second width varies to create a second concave section in the second portion of the anchoring region and to secure the second portion within the sclera.

3. The tack according to claim 1, wherein the post is generally conical in shape, the first end of the post having a point to facilitate puncturing of the tack in the eye.

4. The tack according to claim 1, wherein the post is solid and comprises a drug dispersed in a nonerodible polymeric matrix such that the drug is delivered to the eye by diffusing through the post.

5. The tack according to claim 1, wherein the post is solid and comprises a drug dispersed in an erodible polymeric matrix such that the drug is delivered to the eye by dissolution of the post.

6. The tack according to claim 1, wherein the post comprises a membrane which is at least semi-permeable forming a hollow chamber, the chamber being filled with a liquid drug to be delivered to the eye which passes through the membrane.

7. The tack according to claim 1, wherein the post comprises a solid core which is constructed of a drug, the core being surrounded by a membrane which is at least semi-permeable such that the drug is delivered to the eye by dissolution and diffusion.

8. The tack according to claim 1, wherein the head is flexible.

9. The tack according to claim 8, wherein the head is generally convex and has a generally circular perimeter.

10. The tack according to claim 9, wherein the head is curved to complement a curvature of the eye at a point where the head abuts the eye.

11. A tack for intraocular drug delivery, comprising:

(a) a post including a drug to be administered, the post having a first end and a second end, the first end for being positioned within a vitreous region of an eye, the post having a length measured parallel to a longitudinal axis of the tack, the length being determined according to a dosage of the drug to be administered and such that obstruction of vision through a lens of the eye is minimized;

(b) a central portion affixed to the second end of the post, the central portion for being positioned within at least one of a retina, a choroid and a sclera;

(c) a head extending radially outwardly from the central portion such that upon insertion of the central portion and post within the eye, the head remains external to the eye and abuts a scleral surface of the eye; and (d) a suture hole extending through the head for receiving a suture to anchor the head to the sclera.

12. The tack according to claim 11, wherein the central portion has a constant width, the width being measured perpendicularly to the longitudinal axis of the tack.

13. The tack according to claim 11, wherein the post is generally conical in shape, the first end of the post having a point to facilitate puncturing of the tack in the eye.

14. The tack according to claim 11, wherein the post is solid and comprises a drug dispersed in a nonerodible polymeric matrix such that the drug is delivered to the eye by diffusing through the post.

15. The tack according to claim 11, wherein the post is solid and comprises a drug dispersed in an erodible polymeric matrix such that the drug is delivered to the eye by dissolution of the post.

16. The tack according to claim 11, wherein the post comprises a membrane which is at least semi-permeable forming a hollow chamber, the chamber being filled with a liquid drug to be delivered to the eye which passes through the membrane.

17. The tack according to claim 11, wherein the post comprises a solid core which is constructed of a drug, the core being surrounded by a membrane which is at least semi-permeable such that the drug is delivered by osmosis.

18. The tack according to claim 11, wherein the head is flexible.

19. The tack according to claim 18, wherein the head is generally convex and has a generally circular perimeter.

20. The tack according to claim 19, wherein the head is curved to complement a curvature of the eye at a point where the head abuts the eye.

21. A tack for intraocular drug delivery, comprising:

(a) a post including a membrane which is at least semi-permeable forming a hollow void, the void being filled with a first portion of a liquid drug to be administered, the post having a first end and a second end, the first end for being positioned within a vitreous region of an eye, the post having a length measured parallel to a longitudinal axis of the tack, the length being determined according to a dosage of the drug to be administered and such that obstruction of vision through a lens of the eye is minimized;

(b) a hollow central portion affixed to the second end of the post and being filled with a second portion of the liquid drug to be administered, the hollow central portion being in fluid communication with the void, the central portion for being positioned within at least one of a retina, a choroid and a sclera of the eye; and (c) a head extending radially outwardly from the central portion such that upon insertion of the central portion and the post within the eye, the head remains external to the eye and abuts a scleral surface of the eye, the head having an opening in fluid communication with the hollow central portion for injection of subsequent doses of the liquid drug.

22. The tack according to claim 21, further comprising a removable cap covering the opening in the head.

23. The tack according to claim 21, further comprising an injection port within the opening.

24. The tack according to claim 23, further comprising a removable sterile cover in communication with the injection port.

25. The tack according to claim 21, wherein the central portion has a width measured perpendicularly to a longitudinal axis of the tack, said width varying to provide the central portion with a configuration which anchors the tack within at least one of a sclera, a retina and a choroid.

26. The tack according to claim 21, wherein the head is flexible.

27. The tack according to claim 21, further comprising a suture hole extending through the head for receiving a suture to anchor the head to the sclera.

28. The tack according to claim 21, wherein the head is generally convex and has a generally circular perimeter.

29. The tack according to claim 27, wherein the head is curved to complement a curvature of the eye at a point where the head abuts the eye.

30. A method for insertion and removal of an intraocular device for providing sustained release of a drug, comprising the steps of:

(a) separating a portion of a conjunctival membrane of an eye from a portion of scleral tissue underlying the portion of the conjunctival membrane;

(b) making an incision through the portion of scleral tissue into a vitreous region of the eye such that an opening for insertion of the device is created;

(c) inserting the device into the opening such that a first portion of the device is situated in the vitreous region and a second portion of the device is positioned external to the portion of scleral tissue;

(d) reattaching the portion of the conjunctival membrane to the portion of the scleral tissue underlying the portion of the conjunctival membrane;

(e) maintaining the first portion of the device in the vitreous region until the first portion of the device has delivered a predetermined dosage of the drug into the vitreous region;

(f) separating the portion of the conjunctival membrane from the portion of scleral tissue underlying the portion of the conjunctival membrane;

(g) removing the device from the eye; and (h) reattaching the portion of the conjunctival membrane over the opening in the portion of scleral tissue.

31. The method according to claim 30, further comprising the step of closing the opening in the portion of scleral tissue with a suture material after removing the device.

32. The method according to claim 30, wherein in step (a) the portion of conjunctival membrane is separated from the eye proximate to a ciliary pars plana of the eye.

33. The method according to claim 30, wherein in step (b) the incision made is a full thickness incision.

34. The method according to claim 30, wherein in step (c) the device is inserted by a syringe.

35. The method according to claim 30, further comprising the step of suturing the second portion of the device remaining external to the portion of scleral tissue to the portion of scleral tissue.

36. The method according to claim 30, wherein in step (e) the first portion of the device is maintained in the vitreous region for at least 3 days.

* * * * *